United States Patent [19]
Steinke et al.

[11] Patent Number: 5,549,557
[45] Date of Patent: Aug. 27, 1996

[54] CATHETER BALLOON PROXIMAL HEAT BOND ON EXTENDED SHAFT

[75] Inventors: Thomas A. Steinke; Joseph Gulachenski; R. Thomas Curtis, III, all of San Diego, Calif.

[73] Assignee: Medtronic, Inc., Minneapolis, Minn.

[21] Appl. No.: 286,841

[22] Filed: Aug. 5, 1994

[51] Int. Cl.⁶ .................................................. A61M 29/00
[52] U.S. Cl. ........................... 604/103; 604/96; 604/282; 604/102
[58] Field of Search ................................ 604/96, 97, 101, 604/103, 104, 264, 280, 282, 95, 102

[56] References Cited

U.S. PATENT DOCUMENTS

| | | | |
|---|---|---|---|
| 4,661,095 | 4/1987 | Taller et al. ............................ | 604/103 |
| 4,723,936 | 2/1988 | Buchbinder . | |
| 4,748,982 | 6/1988 | Holzewski . | |
| 4,762,129 | 8/1988 | Bonzel . | |
| 4,782,834 | 11/1988 | Maguire . | |
| 4,917,666 | 4/1990 | Solar . | |
| 4,944,745 | 7/1990 | Sogard et al. ............................ | 604/53 |
| 4,988,356 | 1/1991 | Crittenden . | |
| 5,030,210 | 7/1991 | Alchas ................................... | 604/247 |
| 5,040,548 | 8/1991 | Yock . | |
| 5,046,503 | 9/1991 | Schneiderman ............................ | 604/96 |
| 5,061,273 | 10/1991 | Yock . | |
| 5,100,381 | 3/1992 | Burns . | |
| 5,135,535 | 8/1992 | Kramer . | |
| 5,154,725 | 10/1992 | Leopold . | |
| 5,156,594 | 10/1992 | Keith . | |
| 5,156,595 | 10/1992 | Adams . | |
| 5,180,367 | 1/1993 | Kontos . | |
| 5,232,445 | 8/1993 | Bonzel ................................... | 604/96 |
| 5,263,932 | 11/1993 | Jang ..................................... | 604/96 |
| 5,267,959 | 12/1993 | Forman .................................. | 604/103 |
| 5,290,230 | 3/1994 | Ainsworth . | |
| 5,300,025 | 4/1994 | Wantink ................................. | 604/282 |
| 5,328,472 | 7/1994 | Steinke . | |
| 5,338,295 | 8/1994 | Cornelius et al. ........................ | 604/96 |
| 5,368,567 | 11/1994 | Lee ..................................... | 604/96 |
| 5,433,706 | 7/1995 | Abiuso .................................. | 604/96 |

FOREIGN PATENT DOCUMENTS 9411053  5/1994  WIPO .

*Primary Examiner*—Corrine M. McDermott
*Assistant Examiner*—N. Kent Gring
*Attorney, Agent, or Firm*—Dianne M. D. Plunkett; Harold R. Patton

[57] ABSTRACT

The present invention relates to angioplasty catheters and more particularly, to a proximal balloon bond on an extended shaft comprising an irradiated biocompatable thermoplastic jacket having a necked down distal end with the proximal end of a balloon heat bonded to the distal end of the jacket. In an alternative embodiment the catheter has an irradiated biocompatable thermoplastic jacket having a necked down distal end with the proximal end of a balloon heat bonded to the distal end of the jacket and a core wire extending throughout the jacket and throughout the balloon. In yet another alternative embodiment, the catheter has an irradiated biocompatable thermoplastic jacket having a necked down distal end with the proximal end of a balloon heat bonded to the distal end of the jacket as well as a sleeve defining a guidewire lumen, the sleeve extending longitudinally and exterior to the jacket and balloon. In yet another alternative embodiment, the catheter has an irradiated biocompatable thermoplastic jacket having a necked down distal end with the proximal end of a balloon heat bonded to the distal end of the jacket and a spring coil extending longitudinally within the jacket. In yet another alternative embodiment, the catheter has a biocompatable thermoplastic jacket having a necked down distal end with the proximal end of a balloon heat bonded to the distal end of the jacket and a spring coil extending longitudinally within the jacket.

8 Claims, 3 Drawing Sheets

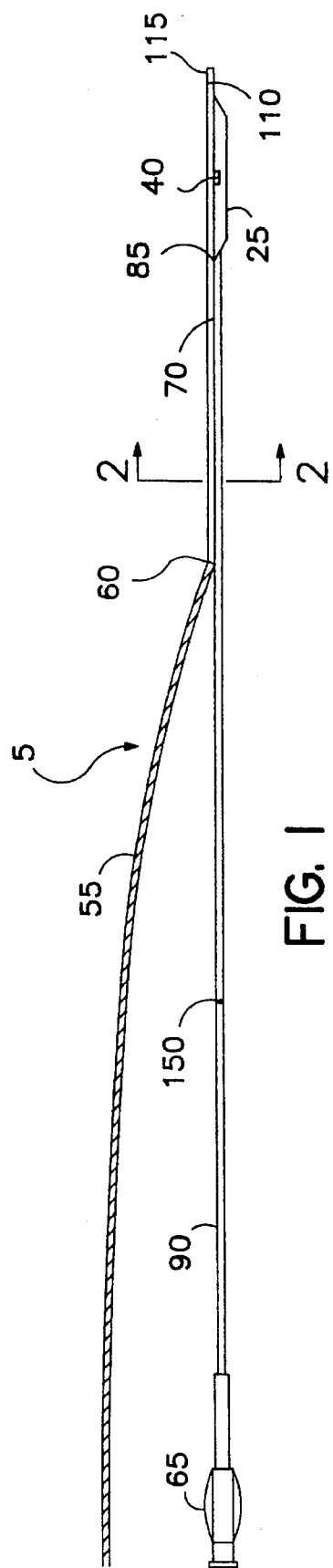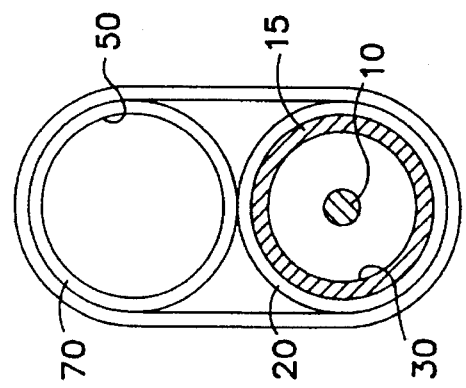

CATHETER BALLOON PROXIMAL HEAT BOND ON EXTENDED SHAFT

FIELD OF THE INVENTION

The present invention relates to angioplasty catheters and more particularly, to a proximal balloon bond on an extended shaft.

BACKGROUND OF THE INVENTION

Catheters are tube-like members inserted into the body for diagnostic or therapeutic reasons. One of the therapeutic procedures applicable to the present invention is known as percutaneous transluminal coronary angioplasty (PTCA). This procedure can be used, for example, to reduce arterial build-up of cholesterol fats or atherosclerotic plaque. Using a movable wire system, one could more readily select the desired coronary artery and reach smaller branches as movable guidewires are smaller and more flexible than the fixed wire systems. The catheter is subsequently tracked over the guidewire to the stenosis. The balloon at the distal end of the catheter is then inflated causing the site of the stenosis to widen. After the balloon is deflated, the catheter is withdrawn over the guidewire and another catheter can be slid into place over it if necessary.

Various versions of rapid exchange catheters, either coaxial or biaxial, are shown in the following patents: U.S. Pat. Nos. 4,762,129 and 5,232,445 issued to Bonzel, U.S. Pat. Nos. 5,040,548 and 5,061,273 issued to Yock, U.S. Pat. No. 4,748,982 issued to Horzewski, et at., U.S. Pat. No. 4,988,356 issued to Crittenden, U.S. Pat. No. 5,135,535 issued to Kramer and U.S. Pat. No. 5,180,367 to Kontos and assignee's WO 94/11053 issued to Ndondo-Lay et at.

The following are examples of spring coil catheters. Some catheters, such as the present assignee's 14K™ catheter and Thruflex® catheter to Solar and Roucher (shown in U.S. Pat. No. 4,917,666) are over-tile-wire catheters having spring coil lumens to improve the pushability of the catheter. At the same time, the spring coil is flexible laterally, with minimized kinking. In the present assignee's Gold X™ catheter, a coaxial rapid exchange catheter shown in U.S. Pat. No. 5,328,472 issued Jul. 12, 1994 to Steinke et at., the outer lumen is similarly made of a spring coil, with a core wire extending through a portion of the coil for added pushability. In the present assignee's Omniflex™ catheter to Buchbinder and Solar (shown generally in U.S. Pat. No. 4,723,936) as sold, a proximal hypotube about 3.81 cm (1.50 inches) long improves the handling of the catheter, which is otherwise formed of a spring coil.

The following illustrates proximal balloon bonds used in the prior art. Adhesives are used in U.S. Pat. No. 4,748,982 to Horzewski et at. (col. 3, lines 18–27); in U.S. Pat. No. 5,100,381 to Burns (bonding, col. 3, lines 16–17); in U.S. Pat. No. 5,154,725 to Leopold (Cyanoacrylate or Loctite™ 405, col. 5, lines 3–6); in U.S. Pat. No. 5,156,594 to Keith (Epoxy or Cyanoacrylate, col. 8 lines 18–21); in U.S. Pat. No. 5,156,595 to Adams (Epoxy, col. 3, lines 35–40); and in U.S. Pat. No. 5,290,230 to Ainsworth et al. (col. 6, lines 25–27).

Heat bonding is used in U.S. Pat. No. 4,782,834 to Maguire (col. 3, lines 48–50). Heat shrinking is used in U.S. Pat. No. 4,748,982 to Horzewski et at. (col. 3, lines 25–27).

What is needed is a method of bonding the proximal end of a balloon which is reliable, which results in a minimal proximal bond profile as well as minimizing manufacturing time. The bonding technique should apply when using dissimilar materials or when using spring coil technology. A flexible bond is desired to allow better tracking.

SUMMARY OF THE INVENTION

The present invention is accomplished by providing a catheter with an irradiated biocompatible thermoplastic jacket having a necked down distal end with the proximal end of a balloon heat bonded to the distal end of the jacket. In an alternative embodiment the catheter has an irradiated biocompatible thermoplastic jacket having a necked down distal end with the proximal end of a balloon heat bonded to the distal end of the jacket and a core wire extending throughout the jacket and throughout the balloon. In yet another alternative embodiment, the catheter has an irradiated biocompatible thermoplastic jacket having a necked down distal end with the proximal end of a balloon heat bonded to the distal end of the jacket as well as a sleeve defining a guidewire lumen, the sleeve extending longitudinally and exterior to the jacket and balloon. In yet another alternative embodiment, the catheter has an irradiated biocompatible thermoplastic jacket having a necked down distal end with the proximal end of a balloon heat bonded to the distal end of the jacket and a spring coil extending longitudinally within the jacket. In yet another alternative embodiment, the catheter has a biocompatible thermoplastic jacket having a necked down distal end with the proximal end of a balloon heat bonded to the distal end of the jacket and a spring coil extending longitudinally within the jacket.

Irradiation renders materials easier to neck down and permits them greater exposure to heat without breakage. When using a jacketed spring coil as a shaft, irradiating the jacket is desirable to render the jacket distendable such that it will fit over the spring coil prior to being heat shrunk down about the spring coil.

It is desirable that balloon bonds not increase the outer diameter of the catheter shaft. Adhesive curing time increases manufacturing time. One part ultraviolet light cure adhesives cure rapidly in about 15 seconds under exposure to ultraviolet light. These are undesirable because they result in a larger profile than does a heat bond. One part ultraviolet cure adhesives can also damage the balloon and may require treating the balloon interior with plasma. Cyanoacrylate and Loctite™ 404 are examples of one part adhesives. Two part adhesives do not require plasma treatment and therefore may not result in deterioration of the balloon interior but do result in a larger profile than does a heat bond. Two part adhesives furthermore increase manufacturing time because of the additional mixing time required as well as the very long curing times required. Epoxy is an example of a two part adhesive.

BRIEF DESCRIPTION OF THE DRAWINGS

FIG. 1 is a side elevational view;

FIG. 2 is a cross-sectional view taken along the line 2—2 in FIG. 1;

DETAILED DESCRIPTION OF THE PREFERRED EMBODIMENTS

Figure 3:
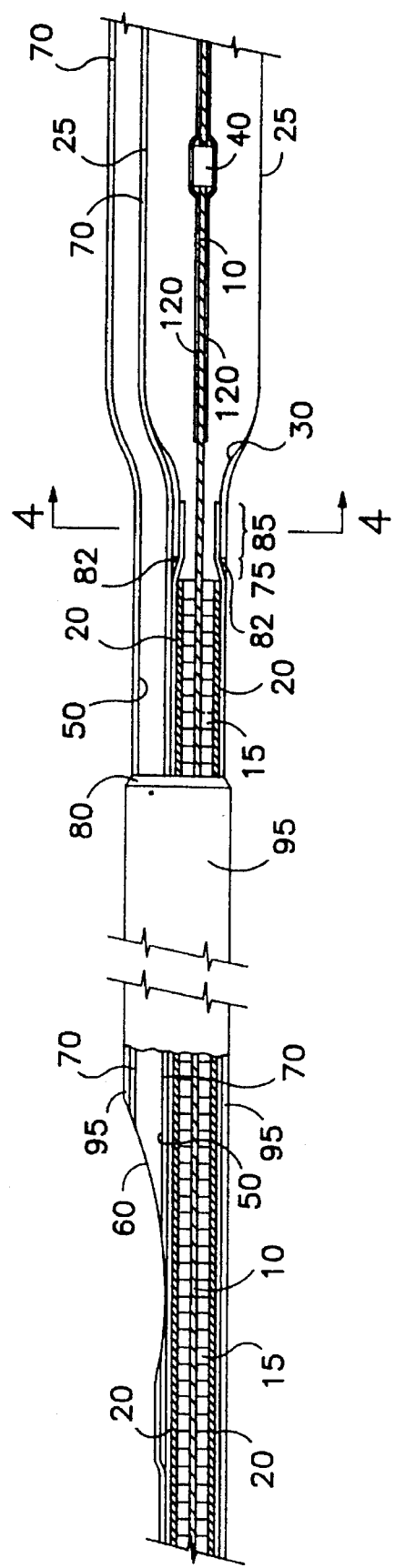
FIG. 3 is a longitudinal cross-sectional view of the area of the proximal bond 85 of FIG. 1.

Although a specific rapid exchange, biaxial lumen, spring coil shaft with a core wire will be described herein, it is understood that Applicant's proximal bond technology could be used with other forms of catheter shaft technology such as a coaxial lumen or a nonspring coil shaft. A spring coil shaft is not required and a conventional shaft with a necked down distal end could be used. Applicant's proximal bond method could also be used in bonding two dissimilar materials.

The advantages of applicant's proximal bond technique include avoiding the use of adhesives at the proximal bond site thereby reducing manufacturing time as well as reducing the catheter diameter at the proximal bond site. Adhesives 80 and 82 are typical one part ultraviolet light cure adhesives such as Loctite™ 3321. Such adhesives cure in about 15 seconds under exposure to ultraviolet light. It is undesirable to use one part ultraviolet adhesives in the proximal bond area 85 because they increase profile. Two part adhesives are undesirable because of the increased profile as well as the added mixing time required and also the very long curing times required. The proximal bonding method avoids the use of both one part and two part adhesives. Applicant's proximal bond 85 results in a balloon 25 neck outer diameter less than or equal to 0.0838 cm or 0.0813 cm for 4.0 mm balloons (0.033 inches or 0.032 inches for 4.0 mm balloons) when implementing a biaxial configuration. The outer diameter of FIG. 4 (from the top of the sleeve 70 to the bottom of balloon 25) is 0.14 cm (0.055 inches).

Referring to FIGS. 1 through 5, the preferred rapid exchange catheter 5 according to the present invention is formed of a shaft, an external guidewire 55 sleeve 70 and a balloon 25. The shaft comprises a hypotube 90 at the proximal end of the shaft which is affixed to a spring coil 15 comprising the distal end of the shaft. The spring coil 15, has a jacket 20 surrounding the coil. The jacket 20 defines the balloon inflation lumen 30. At the proximal end, a handle 65 is attached to the hypotube 90.

The hypotube 90 of FIG. 1 extends at least half the length of the shaft, preferably about two-thirds of the length of the shaft, and the spring coil 15 forms the remainder of the shaft. In the preferred embodiment, the catheter is about 135 cm (53.15 inches) long and the hypotube 90 extends through the proximal 98 cm. The spring coil 15 is sealed and jacketed 20 with polyethylene so that it forms an inflation lumen 30. The stainless steel hypotube 90, is coated for lubricity resulting in a 1.8 fr diameter of 0.6 mm. Coating agents such as fluoropolymers can be used.

The FIGS. 2 and 3 spring coil 15 is approximately 32.5 cm long and has a shaft diameter of 2.2 fr (0.7 mm). The external lumen jacket 95 which encloses both the sleeve 70 and the spring coil 15 has a 3.0 fr shaft outer diameter of 1.2 mm. The spring coil can be brazed 150 to the distal end of hypotube 90. The spring coil 15 extends to the proximal end of balloon 25. Spring coil 15 is a helically wound flat wire preferably made of a biocompatible material such as stainless steel or tungsten and, together with the hypotube, renders the catheter highly pushable. A further advantage of a metal spring coil 15 is that it is visible under fluoroscopy, thereby serving as a proximal balloon 100 marker.

Figure 4:
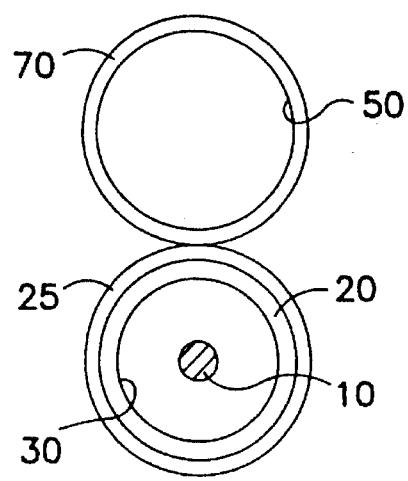
FIG. 4 is a cross-sectional view taken along the line 4—4 in FIG. 3.
Figure 5:
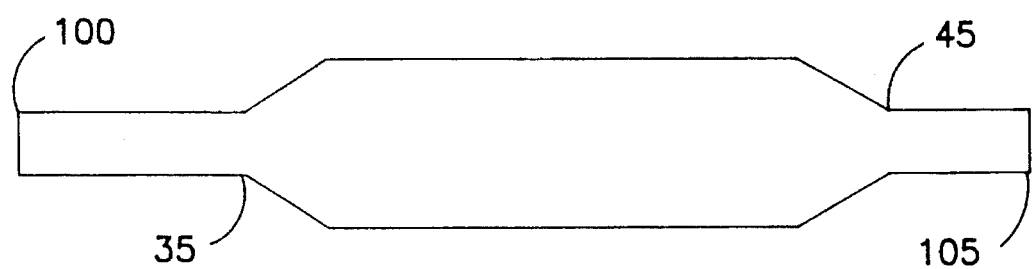
FIG. 5 depicts the balloon cones and tails.

Jacket 20 of FIGS. 2, 3, and 4 coveting spring coil 15 consists of a biocompatible thermoplastic such as polyethylene or polyester. The thermoplastic jacket 20 may be optionally irradiated. Irradiation renders materials easier to neck down and permits them greater exposure to heat without breakage. When using a spring coil shaft, irradiation is necessary because it renders the jacket 20 distendable such that it will fit over the spring coil 15 prior to being heat shrunk about the spring coil 15. In FIG. 4, showing the cross-section of the proximal bond 85, the jacket 20 is necked down to an outer diameter of approximately 0.042 cm (0.0165 inches) and an inner diameter of 0.025 cm (0.010 inches) by inserting a parylene coated hypotube having an approximate outer diameter of 0.025 cm (0.010 inches) and an inner diameter of approximately 0.018 cm (0.007 inches) over the core wire 10. Jacket 20 is heat shrunk at its proximal end to the distal end of hypotube 90 and over the proximal end of spring coil 15.

The balloon 25 of FIGS. 1, 3, 4 and 5 is preferably made of a non-compliant biocompatible material such as polyethylene and is in fluid communication with the inflation lumen 30 which is used to transmit fluids therethrough for purposes of inflating the balloon 25 and reducing the stenosis. Applicant's preferred balloon material is irradiated Low Density Polyethylene (LDPE).

An optional core wire 10 can be attached to hypotube 90 and extends through spring coil 15 and through balloon 25 to the distal end of the catheter to improve pushability and provide added support to the catheter and balloon. Core wire 10 is tapered along its length, from a diameter of about 0.030 cm (0.012 inches) to about 0.010 cm (0.004 inches). Core wire 10 provides stiffness which improves pushability and torquability. In some embodiments the catheter materials are stiff enough to provide sufficient pushability alone, as may be the case with high density polyethylene or polyester. FIG. 2 shows the core wire 10 as being centered within the balloon inflation lumen 30. Those skilled in the art will understand that the core wire 10 moves about within the balloon inflation lumen 30 such that it is not always centered given slacking and bending.

As seen in FIGS. 1 and 3, a radiopaque marker band 40 is bonded to core wire 10 preferably at the center of the balloon 25. The marker band 40 is used to fluoroscopically view the position of the balloon 25 during dilatation to assist the physician in accurately locating the balloon with respect to the shape or morphology of the lesion. Preferred materials for the marker band 40 include gold or platinum or iridium and alloys of these materials such as 90% platinum and 10% iridium. The distal portion of the spring coil 15 may also be fabricated of a radiopaque material such as platinum to make it visible under a fluoroscope. In some embodiments, the marker band 40 may be eliminated and the entire spring coil 15, or just the distal end of the spring coil 15, may be made of radiopaque materials as described above.

Extending generally parallel to the catheter 5 and exterior to balloon 25 is an external guidewire lumen 50 which is defined by sleeve 70 and seen in FIGS. 1, 2, 3 and 4. Sleeve 70 originates proximal to the balloon 25 and continues to the distal end of the catheter forming the distal tip 110. Sleeve 70 slidably receives and directs guidewire 55 during use, the guidewire passing through proximal port 60, through the sleeve and through distal port 115. The sleeve 70 surrounding the external guidewire lumen 50 is laminated to the inflation lumen jacket 20 and adhesively bonded to balloon 25 with an adhesive such as a UV cure Loctite™ #3321. The laminate, preferably low or high density polyethylene, is heat shrunk around sleeve 70. The external lumen jacket 95 ends approximately at the distal end of the spring coil 15. Adhesive 80 is applied to the distal end of jacket 95 to smooth the abrupt transition. The FIG. 3 shrinkage gap 75 is also filled with adhesive 82. An adhesive such as Loctite™ #3321 may be used.

When the catheter is used as a rapid exchange catheter, sleeve 70 is preferably either about 7 cm (2.76 inches) long or about 20 cm (7.87 inches) long. The sleeve can be made of high density polyethylene, polyimide, polyester or nylon, and is preferably polyethylene. A mandrel is placed within the sleeve 70 during the manufacturing process to maintain the shape and proximal port 60. The shorter guidewire lumen promotes easy exchange of the catheter.

A variety of FIG. 1 guidewire 55 sizes can be used with applicant's invention. The guidewire size dictates the inner diameter of sleeve 70. The sleeve 70 inner diameter must be larger than the outer diameter of the guidewire. For example, when a 0.036 cm (0.014 inches) guidewire is used, the inner diameter for sleeve 70 should preferably be about 0.043 cm (0.017 inches), and the outer diameter should be preferably about 0.053 cm (0.021 inches). For a 0.025 cm (0.010 inches) guidewire, the inner diameter may be about 0.033 cm (0.013 inches) and the outer diameter about 0.046 cm (0.018 inches).

The proximal bond 85 is approximately 1 cm (0.394 inches) long. The proximal bond 85 begins approximately 0.5 mm to 1 mm distal to the distal end of the spring coil 15. The space between the proximal bond 85 and the spring coil 15 represents a shrinkage gap 75. For balloons with a 2.0 mm or 2.5 mm diameter, the shrinkage gap 75 will be less than 1.0 mm. For balloons with a 3.0 mm to 4.0 mm diameter, the shrinkage gap 75 will be less than 0.5 mm. The inflation lumen jacket 20 which covers the spring coil 15 continues distally beyond the spring coil 15, and extends 1 cm beyond the shrinkage gap 75. One cm of the proximal end of the balloon 25 overlaps the distal 1 cm of the inflation lumen jacket 20 thus constituting the proximal bond area 85. The distal 1 cm of the inflation lumen jacket 20 is in effect an extended shaft.

The general procedure for creating the proximal bond involves three major steps, necking the balloon 25, sizing the balloon 25 and bonding the proximal end of the balloon 25. Necking the balloon 25 consists of manually stretching the balloon 25 proximal and distal sections over a mandrel, placing the proximal and distal sections in clamps and heating the proximal and distal sections. Sizing the balloon 25 includes placing the balloon 25 proximal and distal sections in a sizing die where it is heated, then trimming the balloon after the sizing operation. The bonding operation consists of sliding the proximal end of the balloon over the distal end of the inflation lumen jacket with a mandrel inserted therethrough. This assembly is then heated in a split die.

The balloon is necked to reduce the outer diameter of the balloon proximal section (between the balloon proximal cone 35 and the balloon proximal tail proximal end 100) and distal section (between the balloon distal cone 45 and the balloon distal tail distal end 105). Necking the balloon 25 consists of manually stretching the balloon 25 proximal and distal sections over a mandrel, placing the proximal and distal sections in clamps and heating the proximal and distal sections. Before the stretching operation, the 4.0 mm balloon proximal section outer diameter is approximately 0.147 cm (0.058 inches ) for example; after the stretching operation, the outer diameter is approximately 0.079 cm (0.031 inches).

The balloon proximal section is necked as follows. A paralene coated mandrel with a 0.046 cm (0.018 inch) outer diameter for balloon sizes 2.0 mm to 3.5 mm or a mandrel with a 0.043 cm (0.017 inch) outer diameter for balloon size 4.0 mm is inserted from the distal end of the balloon 25 and aligned with the proximal cone 35. All balloons could use the 0.043 cm (0.017 mandrel but a 0.046 cm (0.018 inch) mandrel is easier for an operator to insert into the small balloons. After the balloon 25 proximal section has been stretched, the balloon 25 is placed into a fight clamp with the balloon proximal cone 35 aligned with the proximal edge of the fight clamp. A left clamp is placed over the area extending from the balloon proximal tail proximal end 100 to the balloon proximal cone 35. The balloon proximal cone 35 must be protected by the clamp to avoid heat damage to the balloon. A torch is directed at the right and left clamps for 15 seconds. The temperature for 2.0 mm balloons is about 104 degrees celsius (220 degrees Fahrenheit). For 2.5 mm through 4.0 mm balloons, the torch temperature should be about 118 degrees celsius (245 degrees Fahrenheit). The torch is then removed and the balloon allowed to cool for about 15 seconds before removing the balloon 25 from the mandrel.

The balloon distal section is necked as follows. A paralene coated mandrel having an outer diameter of 0.058 cm (0.023 inches) is inserted from the proximal end of the balloon 25 and aligned with the distal cone 45. After the balloon 25 distal section has been stretched, the balloon 25 is placed into a fight clamp with the balloon distal cone 45 aligned with the proximal edge of the fight clamp. A left clamp is placed over the area extending from the balloon distal tail distal end 105 to the balloon distal cone 45. The balloon distal cone 45 must be protected by the clamp to avoid heat damage to the balloon. A torch is directed at the fight and left clamps for 15 seconds. The temperature for 2.0 mm balloons is about 104 degrees celsius (220 degrees Fahrenheit). For 2.5 mm through 4.0 mm balloons, :he torch temperature should be about 118 degrees celsius (245 degrees Fahrenheit). The torch is then removed and the balloon allowed to cool for about 15 seconds before removing the balloon 25 from the mandrel.

The balloon proximal and distal sections are sized to the correct outer diameter by using a one piece sizing die. The sizing die is heated to cream a rounded proximal 35 and distal cone 45. Drawing the balloons 25 through a sizing die gives them a uniform diameter. The proximal section of the balloon extending from the proximal cone 35 to the proximal tail proximal end 100 is loaded into a cold sizing die with a paralene coated 0.043 cm (0.017 inch) outer diameter mandrel loaded a minimum of 10 mm inside the balloon. The distal section of the balloon extending from the distal cone 45 to the distal tail distal end 105 is loaded into a cold sizing die with a paralene coated 0.058 cm (0.023 inch) outer diameter mandrel loaded a minimum of 10 mm inside the balloon. The balloon 25 proximal and distal section outer diameters should be the same size or smaller than the sizing die. The 2.0 mm balloon proximal section outer diameter should be 0.061 cm (0.024 inches) with a distal section outer diameter of 0.071 cm (0.028 inches). 2.5 mm balloon proximal section outer diameter should be 0.066 cm (0.026 inches) with a distal section outer diameter of 0.076 cm (0.030 inches). The 3.0 mm balloon proximal section outer diameter should be 0.071 cm (0.028 inches) with a distal section outer diameter of 0.086 cm (0.034 inches). The 3.5 mm balloon proximal section outer diameter should be 0.076 cm (0.030 inches) with a distal section outer diameter of 0.091 cm (0.036 inches). The 4.0 mm balloon proximal section outer diameter should be 0.081 cm (0.032 inches) with a distal section outer diameter of 0.097 cm (0.038 inches).

Finish sizing the balloon 25, by creating rounded proximal 35 and distal cones 45, as follows. The proximal section (extending from the proximal cone 35 to the proximal tail proximal end 100) sizing die is heated and the balloon proximal section is drawn through the sizing die up to the proximal cone 35. Then the distal section (extending from the distal cone 45 to the distal tail distal end 105) sizing ale is heated and the balloon distal section is drawn through the sizing die up to the distal cone 45. The sizing dies are heated to between approximately 93–129 degrees celsius (200 to 265 degrees fahrenheit) and more preferably to 93 degrees celsius (200 degrees fahrenheit).

After sizing the balloon 25, the balloon proximal section which extends from the proximal cone 35 to the proximal tail proximal end 100 and the distal section which extends from the distal cone 45 to the distal tail distal end 105 are each trimmed to 22 min. This makes it easier for the operator to handle for the following reason. The balloon has been necked to about 25 mm. At 30 mm the outer diameter of the balloon is larger and will not fit into the sizing die. Trimming the proximal and distal sections to a uniform 22 mm removes the guess work when the operator loads the balloon into the sizing die.

The balloon 25 is given a final trimming as follows. The balloon proximal tail 100 is trimmed as measured from the distal balloon cone 45. Balloons of different dimensions have different cone lengths. This presents difficulties in developing a standardized manufacturing process as different length core wires would be required with balloons of different dimensions. To permit a standard length core wire to be used, balloon proximal tails (the balloon portion between the proximal cone 35 and the proximal tail proximal end 100) are cut to different lengths according to the balloon dimension thereby yielding a uniform length of approximately 40.5 mm between the balloon distal cone 45 and proximal tail proximal end 100. With this procedure, core wires of uniform lengths can be used thereby simplifying the manufacturing process.

The balloon 25 proximal end is slid onto the distal end of the inflation lumen jacket 20 up to the spring coil 15. A 0.015 cm (0.006 inch) mandrel is inserted through the balloon 25 and inside/through the distal end of the inflation lumen jacket 20. This mandrel must be correctly in place during bonding for the catheter to inflate and deflate properly. The catheter assembly including the mandrel is placed through the housing/die holder of the appropriate split die set with the spring coil 15 loaded about 1 mm into the split die end and the jacket 20 loaded about 10 mm into the split die end. Each balloon size uses a split die specific to its size. The split die prevents damage to the balloon because heat is directed only at the bond site area of the split die. The split die also keeps the balloon 25 outer diameter from getting larger. The balloon 25 size and the split die inner diameter are related as follows, 2.0 mm balloons use a split die inner diameter of 0.056 cm (0.022 inches), 2.5 mm balloons use a split die inner diameter of 0.064 cm (0.025 inches), 3.0 mm balloons use a split die inner diameter of 0.067 cm (0.027 inches), 3.5 mm balloons use a split die inner diameter of 0.076 cm (0.030 inches), 4.0 mm balloons use a split die inner diameter of 0.081 cm (0.032 inches).

The balloon 25 is now ready to be bonded to the inflation lumen jacket 20 in the area of the proximal bond 85. The temperature to which the proximal bond 85 is heated is a function of the kind of balloon 25 material, the balloon diameter and the length of time the balloon is heated. Lower temperatures can be used as the time is increased. Applicant's preferred balloon material is irradiated Low Density Polyethylene (LDPE). Temperatures over 127 degrees centigrade (260 degrees fahrenheit) should not be used for a sustained period with polyethylene, for example, or the molecular structure will deform. Such high temperatures can be used, however, if the length of time heated is very short.

The balloon 25 is heated in the area of the proximal bond 85 using radio frequency for about 30 seconds. Examples of suitable heating temperatures follow. The temperature to which the balloon 25 is heated depends on the balloon 25 diameter. For example, 2.0 mm balloons are heated to approximately 112 degrees celsius, 2.5 mm balloons are heated to approximately 122 degrees celsius and 3.0 mm to 4.0 mm balloons are heated to approximately 125 degrees celsius.

A hand held air jet is directed at the split die and is used to keep the balloon proximal cone 35 cool by preventing heat transfer from the split die to the proximal cone 35. The hand held air jet utilizes air flow at ambient air temperature and is directed into the proximal cone 35 tail at about a 5 mm distance to reduce the balloon 25 heat damage from the hot die.

After the requisite 30 seconds of heating cool air flow is used to cool the balloon area of the proximal bond 85 to below 30 degrees celsius to prevent damage to the balloon upon removal. The operator should continue running the air jet until the cooling cycle is complete. When the cooling cycle has stopped, the operator should remove the mandrel by carefully holding the proximal bond 85 close to the proximal cone 35 and pulling the mandrel out.

The distal end of the core wire 15 as well as the marker band 40 are enclosed in an irradiated tubing 120 by means of heat shrinking to prevent the marker band 40 from damaging the balloon. The optional irradiation makes bonding the distal end of the balloon to the core wire easier. Tubing 120 may be made of polyethylene or polyester for example. Sleeve 70 and balloon 25 are joined at the distal end. Balloon 25 is wrapped around sleeve 70 and heat shrunk into place.

The preceding specific embodiments are illustrative of the practice of the invention. It is to be understood, however, that other expedients known to those skilled in the art or disclosed herein, may be employed without departing from the spirit of the invention or the scope of the appended claims.

| No. | Component |
|---|---|
| 5 | Balloon Catheter |
| 10 | Core Wire |
| 15 | Spring Coil |
| 20 | Inflation Lumen Jacket |
| 25 | Balloon |
| 30 | Balloon Inflation Lumen |
| 35 | Balloon Proximal Cone |
| 40 | Radiopaque Marker Band |
| 45 | Balloon Distal Cone |
| 50 | External Guidewire Lumen |
| 55 | Guidewire |
| 60 | Proximal Port |
| 65 | Handle |
| 70 | Sleeve |
| 75 | Shrinkage Gap |
| 80 | Adhesive |
| 82 | Adhesive |
| 85 | Proximal Bond |
| 90 | Hypotube |
| 95 | External Lumen Jacket |
| 100 | Balloon Proximal Tail Proximal End |
| 105 | Balloon Distal Tail Distal end |
| 110 | Distal Tip |
| 115 | Distal Port |
| 120 | Tubing |
| 150 | Braze |

What is claimed is:

1. A catheter comprising:

a jacket having an outer surface, a proximal end and a distal end, an inner diameter and an outer diameter, the jacket defining an inflation lumen, the distal end of the jacket being necked down;

a balloon having an outer diameter, a distal end and a proximal end, the proximal end of the balloon being bonded to the distal end of the jacket where the jacket necks down to an area of reduced outer diameter, and the balloon being sealed thereto so that the balloon is in fluid communication with the inflation lumen;

an elongated spring coil having a proximal end and a distal end extending longitudinally within the jacket, the jacket sealingly surrounding the spring coil and the jacket extending distal to the distal end of the spring coil, the balloon is bonded to the jacket distal to the distal end of the spring coil;

a sleeve which defines a guidewire lumen, the sleeve extending longitudinally and exterior to the jacket and balloon, the sleeve extending to the distal end of the balloon and terminating in a proximal port substantially distal of the proximal end of the jacket, but proximal of the balloon, the sleeve being affixed adjacent to the jacket and balloon; and a shrinkage gap between the distal end of the spring coil and the proximal end of the balloon, the shrinkage gap having a proximal end and a distal end, wherein an adhesive is placed on the outer surface of the jacket where the jacket necks down to an area of reduced outer diameter, the adhesive being placed between the proximal and distal ends of the shrinkage gap such that a continuous uniform outer diameter is maintained for the jacket and balloon between the distal end of the spring coil and the proximal end of the balloon.

2. A catheter according to claim 1 further comprising a core wire extending longitudinally through the inflation lumen and the balloon from the proximal end of the jacket to the distal end of the balloon to provide added support to the catheter and to the balloon, the distal end of the jacket necking down to an inner diameter larger than the core wire, the distal end of the balloon being sealingly affixed to the distal end of the core wire.

3. A catheter according to claim 1 wherein the outer diameter of the proximal end of the balloon in the area where the distal end of the jacket is bonded thereto is not greater than 0.0838 cm.

4. A catheter according to claim 1 wherein the jacket extends 1 cm distal to the distal end of the spring coil.

5. A catheter according to claim 1 wherein the balloon is bonded to the jacket beginning 0.5 mm to 1 mm distal to the distal end of the spring coil.

6. A catheter according to claim 1 wherein the proximal 1 cm of the balloon is bonded to the jacket distal to the distal end of the spring coil.

7. A catheter according to claim 1 further comprising the proximal end of the balloon being heat bonded to the distal end of the jacket where the jacket necks down to an area of reduced outer diameter.

8. A catheter according to claim 1 wherein the jacket is made of an irradiated biocompatible thermoplastic.

* * * * *

UNITED STATES PATENT AND TRADEMARK OFFICE
CERTIFICATE OF CORRECTION

PATENT NO. : 5,549,557
DATED : August 27, 1996
INVENTOR(S) : Steinke et al.

It is certified that error appears in the above-indentified patent and that said Letters Patent is hereby corrected as shown below:

Col. 1, Line 38:  "over-tile'wire" should be "over-the-wire"

Col. 3, Line 59:  "coveting spring" should be "covering spring"

Col. 6, Line 2:   "fight" should be "right"

Col. 6, Line 4:   "fight" should be "right"

Col. 6, Line 21:  "fight" should be "right"

Col. 6, Line 22:  "fight" should be "right"
Col. 6, Line 26:  "fight" should be "right"

Col. 6, Line 29:  ":he" should be "the"

Col. 7, Line 12:  "22min." should be "22mm"

Col. 8, Line 61:  "Distal end" should be "Distal End"

Col. 8, Line 17:  "heating" should be "heating,"

UNITED STATES PATENT AND TRADEMARK OFFICE
CERTIFICATE OF CORRECTION

PATENT NO. : 5,549,557
DATED : August 27, 1996
INVENTOR(S) : Steinke, et al

It is certified that error appears in the above-indentified patent and that said Letters Patent is hereby corrected as shown below:

Abstract, lines 3,7,12,18,22: "biocompatable" should be "biocompatible"

Column 7, line 2: "ale" should be "die"

Signed and Sealed this

Fourteenth Day of October, 1997

*Attest:*

BRUCE LEHMAN

*Attesting Officer*    Commissioner of Patents and Trademarks